US00PP36813P2

(12) United States Plant Patent
Ault

(10) Patent No.: US PP36,813 P2
(45) Date of Patent: Jul. 8, 2025

(54) ***PANICUM* PLANT NAMED 'Blue Lime'**

(50) Latin Name: ***Panicum* hybrid**
Varietal Denomination: Blue Lime

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 0 days.

(21) Appl. No.: 19/010,053

(22) Filed: Jan. 5, 2025

(51) Int. Cl.
*A01H 5/12* (2018.01)
*A01H 6/00* (2018.01)

(52) U.S. Cl.
USPC ..... Plt./384
CPC ..... *A01H 6/00* (2018.05)

(58) Field of Classification Search
USPC ..... Plt./384
CPC ..... A01H 5/12
See application file for complete search history.

*Primary Examiner* — Kent L Bell
(74) *Attorney, Agent, or Firm* — Penny J. Aguirre

(57) ABSTRACT

A new cultivar of *Panicum* plant named 'Blue Lime' that is characterized by its abundant panicles that are large, and airy, its inflorescences with unique glumes that retain their golden yellow-green color 1 to 2 weeks later in the season compared to what is typical for *Panicum* cultivars known to the inventor, and its upright, vase-shaped plant habit with no lodging or splaying stems.

2 Drawing Sheets

Botanical classification: *Panicum* hybrid.
Varietal denomination: 'Blue Lime'.

BACKGROUND OF THE INVENTION

The present invention relates to a new and distinct cultivar of *Panicum* hybrid and will be referred to hereafter by its cultivar name, 'Blue Lime'. 'Blue Lime' represents a new cultivar of switchgrass, an ornamental grass grown for landscape use.

The new cultivar of *Panicum* was derived from an ongoing controlled breeding program conducted by the Inventor in Glencoe, Illinois. The goal of the breeding program was to develop new cultivars of *Panicum* with novel ornamental traits that are well adapted to the upper Midwest as well as other climates.

'Blue Lime' originated as a cross between *Panicum amarum* 'Dewey Blue' (not patented) as the female parent and *Panicum* 'Bad Hair Day' (U.S. Plant Pat. No. 29,313) as the male parent in August of 2017. 'Blue Lime' was selected as a single unique plant in August of 2021 from amongst the resulting seedlings.

Asexual propagation of the new cultivar was first accomplished by the Inventor by rhizome division in Glencoe, Illinois, in April of 2022. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Blue Lime' as a unique cultivar of *Panicum*.

1. 'Blue Lime' exhibits abundant panicles that are large, and wispy.
2. 'Blue Lime' exhibits inflorescences with unique glumes that retain their golden yellow-green color 1 to 2 weeks later in the season compared to what is typical for *Panicum* cultivars known to the inventor.
3. 'Blue Lime' exhibits an upright, vase-shaped plant habit with no lodging or splaying stems.

The male parent of 'Blue Lime' differs from 'Blue Lime' in having a taller and wider plant size, foliage that is greener in color, and darker and less bright yellow glumes on the inflorescences. The female parent of 'Blue Lime' differs from 'Blue Lime' in having a less wide plant size, foliage that is more blue in color, and darker and less bright yellow glumes on the inflorescences. 'Blue Lime' can be most closely compared to *Panicum virgatum* cultivars, 'Northwind' (not patented), and 'Niagara Falls' (U.S. Plant Pat. No. 34,509). 'Northwind' is similar to 'Blue Lime' in having a similar plant size and plant habit and foliage that is blue-green in color. 'Northwind' differs from 'Blue Lime' in having less dense and less abundant inflorescences, darker and less bright yellow glumes that turn pink in color, and foliage and inflorescences that are more vertical and less nodding. 'Niagara Falls' is similar to 'Blue Lime' in having a similar plant width, leaf color, and wispy inflorescences. 'Niagara Falls' is different from 'Blue Lime' in having a shorter plant size, a less columnar plant habit, foliage that is less upright and more pendulous, and glumes that are lighter yellow in color.

BRIEF DESCRIPTION OF THE DRAWINGS

The accompanying color photographs illustrate the overall appearance and distinct characteristics of the new *Pani-*

*cum*. The photographs were taken of a three-year-old plant of 'Blue Lime' as grown outdoors in a trail garden in Glencoe, Illinois.

Figure 1:
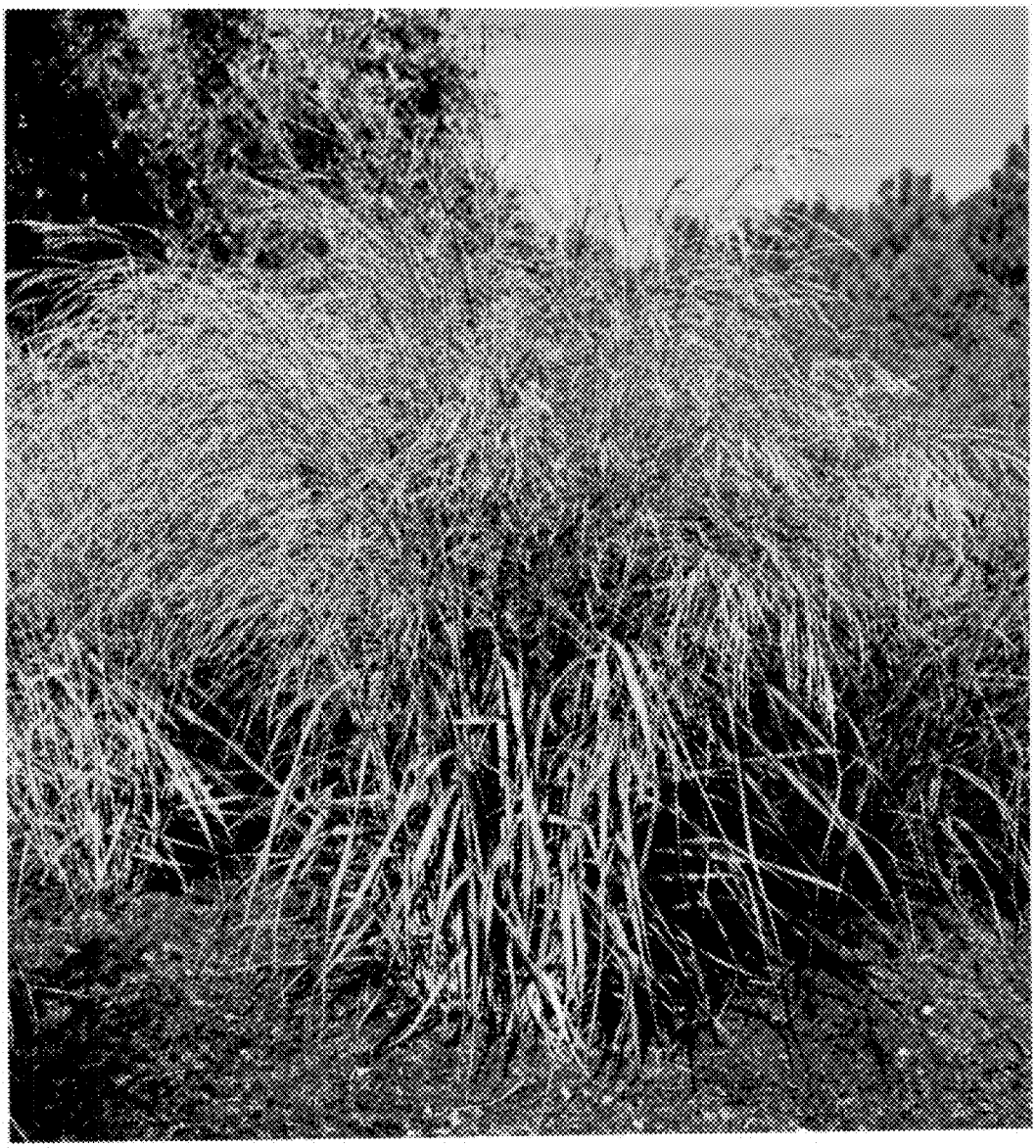

The photograph in FIG. 1 provides a side view of the overall plant habit of 'Blue Lime'.

Figure 2:
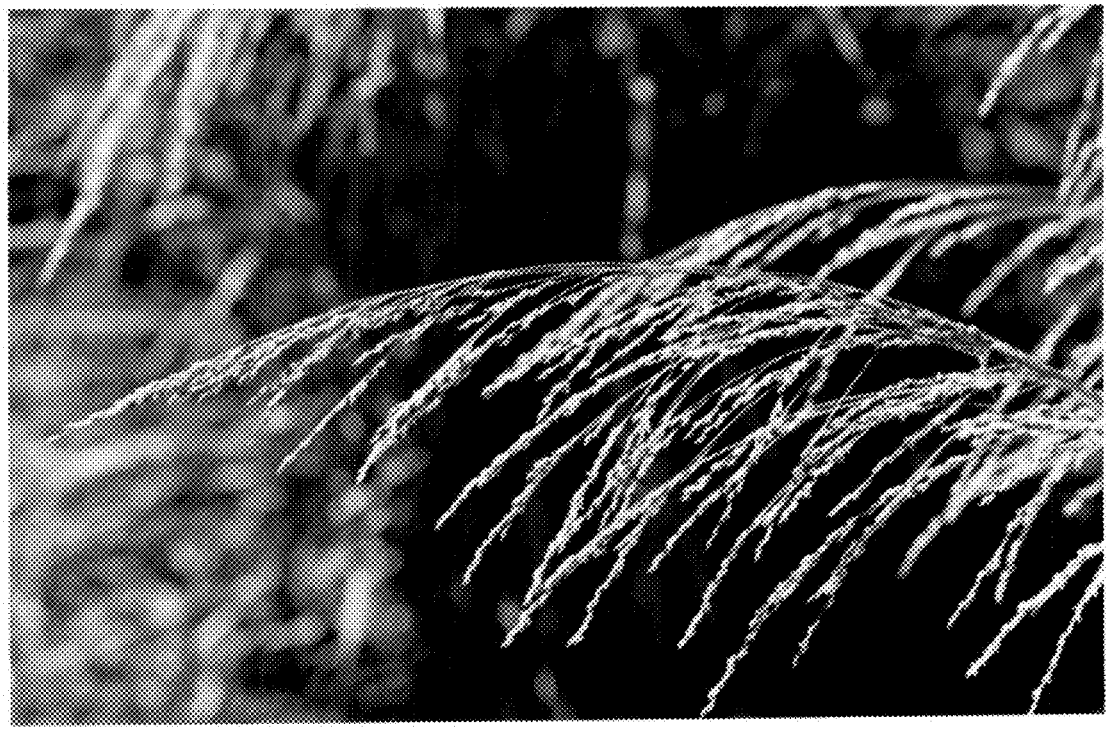

The photograph in FIG. 2 provides a close-up view of inflorescences of 'Blue Lime'.

The colors in the photographs are as close as possible with the photographic and printing technology utilized and the color values cited in the Detailed Botanical Description accurately describe the colors of the new *Panicum*.

DETAILED BOTANICAL DESCRIPTION OF THE PLANT

The following is a detailed description of three-month-old plants of the new cultivar as grown outdoors in 1-qt containers in Glencoe, Illinois. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 6 weeks from early August to late September in Illinois.

*Plant type*.—Herbaceous perennial grass.

*Plant habit*.—Upright, compact.

*Height and width or spread*.—An average of 20 cm in height and 7 cm in spread as a 3-month-old plant as grown in a container, an average of 1.7 m in height (in bloom) and 1.4 m in spread as a 3-year-old plant in the landscape.

*Hardiness*.—At least in U.S.D.A. Zones 4 to 8.

*Diseases and pests*.—Some susceptibility to switchgrass rust (caused by *Puccinia emaculata*) has been observed, no resistance or susceptibility to pests has been observed.

*Root description*.—Fibrous and fine, deeply rooted, 164A in color.

*Propagation*.—Rhizome division.

*Rhizomes*.—An average of 1 cm in length and 2 cm width, 155A in color.

*Growth rate*.—Moderate.

*Time required for root development*.—Time required to produce a young plant; 6 weeks from divided plantlet.

Culm (stem) description:

*General*.—Cylindrical, hollow pith, thin but strong, held erect.

*Culm number*.—An average of 8 in an 8-cm container, forming a tight clump.

*Culm color*.—138A and 143B.

*Culm size*.—An average of 5 mm in diameter and 54 cm in height from the base to the base of the peduncle.

*Culm surface*.—Glabrous, matte, and slightly striate.

*Internode length*.—An average of 11 cm.

Foliage description:

*Leaf shape*.—Narrowly lanceolate.

*Leaf division*.—Simple.

*Leaf margin*.—Entire, scaberulous.

*Leaf base*.—Sheathed to base of the node.

*Leaf venation*.—Parallel, outer veins not distinguishable in color from leaf coloration, both surfaces of center vein transparent and 145B.

*Leaf size*.—At widest point; 1 cm in width, blade; an average of 26 cm in length, sheathed portion; an average of 11 cm.

*Leaves per culm*.—An average of 4 on flowering culms.

*Leaf color*.—Young both surfaces; 144B, mature both surfaces; NN137B.

*Leaf surface*.—Young both surfaces; slightly glossy, glabrous, mature both surfaces; glabrous, matte, and slightly striate.

*Ligule*.—Very sparse, an average of 0.5 mm in height and 1.8 mm in width, all surfaces 157B in color, surfaces covered in soft, fine hairs protruding from the top; 0.5 mm in length, 157B in color.

Flower description:

*Inflorescence type*.—Dense, spreading panicle at terminus of stem, symmetrical, typically 6-flowered spikelet with lower spikelet male and upper spikelet hermaphroditic.

*Inflorescence color*.—144A.

*Inflorescence size*.—An average of 25 cm in length and 20 cm in width.

*Inflorescence arrangement*.—Upright.

*Spikelet description*.—An average of 10 per panicle, elliptic in shape, an average of 1.5 mm in length and 1 mm in width, lower glume; an average of 2 mm in length and 1 mm in width, upper glume and lower lemma; an average of 5 mm in length and 1 mm width, color; glumes and lemma upper and lower surface 160C, palea; an average of 1.5 mm in length and 0.5 mm in width, translucent and glossy, 160C in color, glumes, lemma, and palea are oval to elliptic in shape and convex with all surfaces glabrous and smooth.

*Rachis*.—An average of 9 cm in length from last leaf, raceme portion; an average of 15 cm in length and 1.5 mm in width, glabrous and smooth surface, 138A in color, lateral branches (peduncle-like); an average of 10, about 0.2 mm in width and an average of 15 cm in length (shortest at terminus), 138A in color, glabrous surface, pedicel; an average of 4 mm in length and 0.2 mm in width, very fine and wiry, 138A in color, glabrous surface.

Reproductive organs:

*Androecium*.—Anthers; 3, an average of 1.5 mm in length, 0.5 mm in width, 172A in color, filament; basifixed, very fine, translucent, pollen; moderate in quantity and 162C in color.

*Gynoecium*.—Pistil; 1, stigmas; 2, plumose on short fine styles adnate to ovary, N79B to N79C in color, an average of 2 mm in length and 0.5 mm in width, ovary; 1-locular, superior, an average of 3 mm in length and 0.5 mm in with, 149D in color.

It is claimed:

1. A new and distinct cultivar of *Panicum* plant named 'Blue Lime' as herein illustrated and described.

* * * * *